United States Patent
Agarwal et al.

(10) Patent No.: US 10,720,227 B2
(45) Date of Patent: Jul. 21, 2020

(54) METHOD AND DEVICE FOR MUTATION PRIORITIZATION FOR PERSONALIZED THERAPY

(71) Applicant: Samsung Electronics Co., Ltd., Suwon-si, Gyeonggi-do (KR)

(72) Inventors: Garima Agarwal, Ghaziabad (IN); Srikanth Rama Mallavarapu, Bangalore (IN); Ajit Shyamsunder Bopardikar, Bangalore (IN); Taejin Ahn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 761 days.

(21) Appl. No.: 15/159,546

(22) Filed: May 19, 2016

(65) Prior Publication Data
US 2017/0046478 A1 Feb. 16, 2017

(30) Foreign Application Priority Data

Aug. 12, 2015 (IN) .......................... 4206/CHE/2015
Nov. 3, 2015 (KR) ........................ 10-2015-0153809

(51) Int. Cl.
*G16H 10/60* (2018.01)
*G16B 30/00* (2019.01)
*G16H 10/20* (2018.01)
*G06N 5/02* (2006.01)

(52) U.S. Cl.
CPC .............. *G16B 30/00* (2019.02); *G06N 5/025* (2013.01); *G16H 10/20* (2018.01)

(58) Field of Classification Search
USPC ........................................................ 705/2, 3
See application file for complete search history.

(56) References Cited

U.S. PATENT DOCUMENTS

| | | | | |
|---|---|---|---|---|
| 5,574,828 A * | 11/1996 | Hayward | ............... | G16H 50/20 706/45 |
| 6,532,462 B2 * | 3/2003 | Balaban | ............... | C12Q 1/6809 |
| 2010/0130527 A1 | 5/2010 | Lehrer et al. | | |
| 2011/0098193 A1* | 4/2011 | Kingsmore | .......... | C12Q 1/6869 506/9 |
| 2012/0016594 A1* | 1/2012 | Christman | ............. | G16B 50/00 702/19 |
| 2012/0208706 A1 | 8/2012 | Downing et al. | | |

(Continued)

OTHER PUBLICATIONS

Euan A Ashley et al., Clinical assessment incorporating a personal genome, Lancet 2010: 1525-35 (Year: 2010).*

*Primary Examiner* — Jason S Tiedeman
*Assistant Examiner* — Joshua B Blanchette
(74) *Attorney, Agent, or Firm* — Leydig, Voit & Mayer, Ltd.

(57) ABSTRACT

Provided are methods and devices for mutation prioritization, which are helpful in personalized therapy of a patient. Also, provided are methods and devices for generating a disease knowledgebase. Information present in various categories of knowledge sources with respect to a particular association of <Disease, Gene, Mutation> set may be identified. The identified information is ranked with respect to the disease knowledgebase to find out the most relevant ones for the treatment of a particular Disease/Gene/Mutation of a patient, thereby enabling medical experts to personalize a therapy to be administered to a patient.

7 Claims, 11 Drawing Sheets

ORIGINAL FREQUENCY TABLE

| Sno | GENE | MUTATION | CLINICAL TRIALS | | | | THERAPIES | | | |
|---|---|---|---|---|---|---|---|---|---|---|
| | | | CT0 | CT1 | CT2 | CT3 | T0 | T1 | T2 | T3 |
| 1 | ATP6AP2 | K205E | 0 | 1 | 0 | 0 | 2 | 4 | 2 | 1 |
| 2 | CCDC136 | E135K | 4 | 2 | 1 | 0 | 4 | 1 | 3 | 2 |
| 3 | CD47 | K57N | 3 | 4 | 0 | 1 | 4 | 2 | 1 | 3 |
| 4 | ERCC6 | K954K | 1 | 4 | 2 | 1 | 3 | 2 | 1 | 3 |
| 5 | IL31 | T26M | 2 | 2 | 3 | 1 | 5 | 2 | 3 | 1 |
| 6 | PIK3R1 | L196V | 4 | 2 | 3 | 4 | 5 | 4 | 3 | 2 |
| 7 | PIK3R1 | L166V | 5 | 2 | 3 | 4 | 5 | 2 | 3 | 1 |
| 8 | TP53BP1 | G1186E | 4 | 0 | 3 | 1 | 3 | 4 | 2 | 1 |
| 9 | ERBB2 | S310F | 0 | 4 | 2 | 3 | 0 | 1 | 1 | 1 |
| 10 | ZFAT | M24V | 0 | 0 | 0 | 0 | 2 | 3 | 2 | 1 |

SORTED FREQUENCY TABLE

| Sno | GENE | MUTATION | CLINICAL TRIALS | | | | THERAPIES | | | |
|---|---|---|---|---|---|---|---|---|---|---|
| | | | CT0 | CT1 | CT2 | CT3 | T0 | T1 | T2 | T3 |
| 7 | PIK3R1 | L166V | 5 | 2 | 3 | 4 | 5 | 2 | 3 | 1 |
| 6 | PIK3R1 | L196V | 4 | 2 | 3 | 4 | 5 | 4 | 3 | 2 |
| 2 | CCDC136 | E135K | 4 | 2 | 1 | 0 | 4 | 1 | 3 | 2 |
| 8 | TP53BP1 | G1186E | 4 | 0 | 3 | 1 | 3 | 4 | 2 | 1 |
| 3 | CD47 | K57N | 3 | 4 | 0 | 1 | 4 | 2 | 1 | 3 |
| 5 | IL31 | T26M | 2 | 2 | 3 | 1 | 5 | 2 | 3 | 1 |
| 4 | ERCC6 | K954K | 1 | 4 | 2 | 1 | 3 | 2 | 1 | 3 |
| 9 | ERBB2 | S310F | 0 | 4 | 2 | 3 | 0 | 1 | 1 | 1 |
| 1 | ATP6AP2 | K205E | 0 | 1 | 0 | 0 | 2 | 4 | 2 | 1 |
| 10 | ZFAT | M24V | 0 | 0 | 0 | 0 | 2 | 3 | 2 | 1 |

(56) References Cited

U.S. PATENT DOCUMENTS

| | | | |
|---|---|---|---|
| 2013/0268290 A1* | 10/2013 | Jackson | G16B 50/00 705/2 |
| 2014/0019061 A1* | 1/2014 | Ahn | G16B 5/00 702/19 |
| 2014/0046696 A1* | 2/2014 | Higgins | G06F 19/3456 705/3 |
| 2014/0325587 A1* | 10/2014 | Nilsson | G16B 50/00 726/1 |
| 2016/0283484 A1* | 9/2016 | Chandratillake | G06F 16/24578 |

* cited by examiner

FIG. 5

ORIGINAL FREQUENCY TABLE

| Sno | GENE | MUTATION | CLINICAL TRIALS | | | | THERAPIES | | | |
|---|---|---|---|---|---|---|---|---|---|---|
| | | | CT0 | CT1 | CT2 | CT3 | T0 | T1 | T2 | T3 |
| 1 | ATP6AP2 | K205E | 0 | 1 | 0 | 0 | 2 | 4 | 2 | 1 |
| 2 | CCDC136 | E135K | 4 | 2 | 1 | 0 | 4 | 1 | 3 | 2 |
| 3 | CD47 | K57N | 3 | 4 | 0 | 1 | 4 | 2 | 1 | 3 |
| 4 | ERCC6 | K954K | 1 | 4 | 2 | 1 | 3 | 2 | 1 | 3 |
| 5 | IL31 | T26M | 2 | 2 | 3 | 1 | 5 | 2 | 3 | 1 |
| 6 | PIK3R1 | L196V | 4 | 2 | 3 | 4 | 5 | 4 | 3 | 2 |
| 7 | PIK3R1 | L166V | 5 | 2 | 3 | 4 | 5 | 2 | 3 | 1 |
| 8 | TP53BP1 | G1186E | 4 | 0 | 3 | 1 | 3 | 4 | 2 | 1 |
| 9 | ERBB2 | S310F | 0 | 4 | 2 | 3 | 0 | 1 | 1 | 1 |
| 10 | ZFAT | M24V | 0 | 0 | 0 | 0 | 2 | 3 | 2 | 1 |

SORTED FREQUENCY TABLE

| Sno | GENE | MUTATION | CLINICAL TRIALS | | | | THERAPIES | | | |
|---|---|---|---|---|---|---|---|---|---|---|
| | | | CT0 | CT1 | CT2 | CT3 | T0 | T1 | T2 | T3 |
| 7 | PIK3R1 | L166V | 5 | 2 | 3 | 4 | 5 | 2 | 3 | 1 |
| 6 | PIK3R1 | L196V | 4 | 2 | 3 | 4 | 5 | 4 | 3 | 2 |
| 2 | CCDC136 | E135K | 4 | 2 | 1 | 0 | 4 | 1 | 3 | 2 |
| 8 | TP53BP1 | G1186E | 4 | 0 | 3 | 1 | 3 | 4 | 2 | 1 |
| 3 | CD47 | K57N | 3 | 4 | 0 | 1 | 4 | 2 | 1 | 3 |
| 5 | IL31 | T26M | 2 | 2 | 3 | 1 | 5 | 2 | 3 | 1 |
| 4 | ERCC6 | K954K | 1 | 4 | 2 | 1 | 3 | 2 | 1 | 3 |
| 9 | ERBB2 | S310F | 0 | 4 | 2 | 3 | 0 | 1 | 1 | 1 |
| 1 | ATP6AP2 | K205E | 0 | 1 | 0 | 0 | 2 | 4 | 2 | 1 |
| 10 | ZFAT | M24V | 0 | 0 | 0 | 0 | 2 | 3 | 2 | 1 |

FIG. 6

ORIGINAL FREQUENCY TABLE

| Sno | GENE | MUTATION | CLINICAL TRIALS | | | | THERAPIES | | | |
|---|---|---|---|---|---|---|---|---|---|---|
| | | | CT0 | CT1 | CT2 | CT3 | T0 | T1 | T2 | T3 |
| 1 | ATP6AP2 | K205E | 0 | 1 | 0 | 0 | 2 | 4 | 2 | 1 |
| 2 | CCDC136 | E135K | 4 | 2 | 1 | 0 | 4 | 1 | 3 | 2 |
| 3 | CD47 | K57N | 3 | 4 | 0 | 1 | 4 | 2 | 1 | 3 |
| 4 | ERCC6 | K954K | 1 | 4 | 2 | 1 | 3 | 2 | 1 | 3 |
| 5 | IL31 | T26M | 2 | 2 | 3 | 1 | 5 | 2 | 3 | 1 |
| 6 | PIK3R1 | L196V | 4 | 2 | 3 | 4 | 5 | 4 | 3 | 2 |
| 7 | PIK3R1 | L166V | 5 | 2 | 3 | 4 | 5 | 2 | 3 | 1 |
| 8 | TP53BP1 | G1186E | 4 | 0 | 3 | 1 | 3 | 4 | 2 | 1 |
| 9 | ERBB2 | S310F | 0 | 4 | 2 | 3 | 0 | 1 | 1 | 1 |
| 10 | ZFAT | M24V | 0 | 0 | 0 | 0 | 2 | 3 | 2 | 1 |

SORTED FREQUENCY TABLE

| Sno | GENE | MUTATION | CLINICAL TRIALS | | | | THERAPIES | | | |
|---|---|---|---|---|---|---|---|---|---|---|
| | | | CT0 | CT1 | CT2 | CT3 | T0 | T1 | T2 | T3 |
| 6 | PIK3R1 | L196V | 4 | 2 | 3 | 4 | 5 | 4 | 3 | 2 |
| 7 | PIK3R1 | L166V | 5 | 2 | 3 | 4 | 5 | 2 | 3 | 1 |
| 5 | IL31 | T26M | 2 | 2 | 3 | 1 | 5 | 2 | 3 | 1 |
| 3 | CD47 | K57N | 3 | 4 | 0 | 1 | 4 | 2 | 1 | 3 |
| 2 | CCDC136 | E135K | 4 | 2 | 1 | 0 | 4 | 1 | 3 | 2 |
| 8 | TP53BP1 | G1186E | 4 | 0 | 3 | 1 | 3 | 4 | 2 | 1 |
| 4 | ERCC6 | K954K | 1 | 4 | 2 | 1 | 3 | 2 | 1 | 3 |
| 1 | ATP6AP2 | K205E | 0 | 1 | 0 | 0 | 2 | 4 | 2 | 1 |
| 10 | ZFAT | M24V | 0 | 0 | 0 | 0 | 2 | 3 | 2 | 1 |
| 9 | ERBB2 | S310F | 0 | 4 | 2 | 3 | 0 | 1 | 1 | 1 |

METHOD AND DEVICE FOR MUTATION PRIORITIZATION FOR PERSONALIZED THERAPY

CROSS-REFERENCE TO RELATED APPLICATIONS

This application claims the benefit of Indian Patent Application No. 4206/CHE/2015, filed on Aug. 12, 2015, in the Controller General of Patents Designs and Trademarks, and Korean Patent Application No. 10-2015-0153809, filed on Nov. 3, 2015, in the Korean Intellectual Property Office, the disclosures of which are incorporated by reference herein in their entirety.

BACKGROUND

1. Field

The present disclosure relates to clinical genomics, and more particularly, to methods and devices for mutation prioritization for personalized therapy.

2. Description of the Related Art

Next generation sequencing (NGS)-based personalized diagnostics hold great potential as a valuable tool for clinical decision making in healthcare. Its market is currently estimated to be 393 million USD and is expected to grow at a fast pace in coming years. The emphasis of personalized diagnostics has been on genetic disorders, especially on cancer. With 1 million cancer cases being diagnosed annually in the US alone and poor response rates (about 25%) to generic treatments, NGS-based diagnostics may have a significant impact on prescribing effective treatment to an individual.

Such personalized diagnostics are based on analysis of a set of mutations obtained by analyzing DNA data of individuals through a NGS analysis pipeline. These mutations, which characterize an individual's disease, help clinicians in tailoring therapy to the individual's disease. Although very promising, several challenges need to be addressed before mutation data becomes useful for personalized therapy. A key issue is to organize often unstructured data such as mutation-disease association or cancer-specific targeted therapy information into a structured format for automated analysis. Systematic organization of relevant information plays a vital role in data-driven approaches that leverage existing knowledge to recommend therapy options to clinicians and researchers.

Existing approaches often focus on therapies and on prioritizing the therapies. Evidence used in these approaches is extracted and curated from similar knowledge sources as used in the present disclosure. This evidence can include, clinical trials and publications supporting the use of a particular therapy, among other sources. In addition, biomarker data can also used. In other approaches, mutations are classified using evidence from sources such as publications into different classes based on the evidence contained in the publication.

Thus, there exists a need for a method that considers a user specified knowledgebase, obtains mutations of a patient, prioritize mutations based on data gathered from the knowledgebase, and assists in deciding treatment options for the patient based on information gathered regarding one or more mutations in question.

SUMMARY

Provided are methods and devices for mutation prioritization for personalized therapy.

Additional aspects will be set forth in part in the description which follows and, in part, will be apparent from the description, or may be learned by practice of the presented embodiments.

According to an aspect of an embodiment, a method for mutation prioritization for personalized therapy is provided. The method typically includes acquiring mutation information of a patient to be treated, wherein the mutation information includes information associated with at least one of a disease, a gene, and an alteration of genomic DNA, mapping the acquired mutation information with a disease knowledgebase, forming mapped mutation information by identifying at least one of the disease, the gene, and the alteration of genomic DNA, the mapped mutation information being mapped with data points in the disease knowledgebase, generating a frequency table according to categories of a knowledge source and classes in the categories, based on the mapped mutation information, and prioritizing the mapped mutation information in the frequency table based on a prioritization scheme.

According to an aspect of another embodiment, a device for mutation prioritization for personalized therapy is provided. The device typically includes a memory, and at least one processor coupled to the memory, wherein the at least one processor is configured to acquire mutation information of a patient to be treated, wherein the mutation information includes information associated with at least one of a disease, a gene, and an alteration of genomic DNA, map the acquired mutation information with a disease knowledgebase, form mapped mutation information by identifying at least one of the disease, the gene, and the alteration of genomic DNA, the mapped mutation information being mapped with data points in the disease knowledgebase, generate a frequency table according to categories of a knowledge source and classes in the categories, based on the mapped mutation information, and prioritize the mapped mutation information in the frequency table based on a prioritization scheme.

According to an aspect of another embodiment, a method of generating a disease knowledgebase is provided. The method typically includes acquiring information pertaining to at least one of a disease, a gene, an alternation of genomic DNA, and a parameter of clinical relevance from at least one knowledge source falling under at least one category, curating the obtained information to extract at least one data point indicative of at least one of the disease, the gene, the alteration of genomic DNA, and the parameter of clinical relevance from the at least one knowledge source, forming data of associations of the at least one data point by identifying associations of data points indicative of the disease, the gene, and the alteration of genomic DNA with data points indicative of the parameter of clinical relevance, classifying the associations of the at least one data point into at least one class, for linkage with the disease, the gene, and the alteration of genomic DNA, and generating the disease knowledgebase based on the classified associations of the at least one data point in the at least one category.

According to an aspect of another embodiment, a device for generating a disease knowledgebase is provided. The device typically includes a memory, and at least one processor coupled to the memory, wherein the at least one processor is configured to acquire information pertaining to at least one of a disease, a gene, an alternation of genomic DNA, and a parameter of clinical relevance from at least one knowledge source falling under at least one category, curate the obtained information to extract at least one data point indicative of at least one of the disease, the gene, the alteration of genomic DNA, and the parameter of clinical relevance from the at least one knowledge source, form data of associations of the at least one data point by identifying associations of data points indicative of the disease, the gene, and the alteration of genomic DNA with data points indicative of the parameter of clinical relevance, classify the associations of the at least one data point into at least one class, for linkage with the disease, the gene, and the alteration of genomic DNA, and generate the disease knowledgebase based on the classified associations of the at least one data point in the at least one category.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

These and/or other aspects will become apparent and more readily appreciated from the following description of the embodiments, taken in conjunction with the accompanying drawings in which:

FIG. 5 is a diagram for describing sorting of mutations based on a higher clinical trial evidence value than a therapy evidence value, according to an embodiment;

FIG. 6 is a diagram for describing sorting of mutations based on a higher therapy evidence value than a clinical trial evidence value, according to an embodiment;

DETAILED DESCRIPTION

Figure 1:
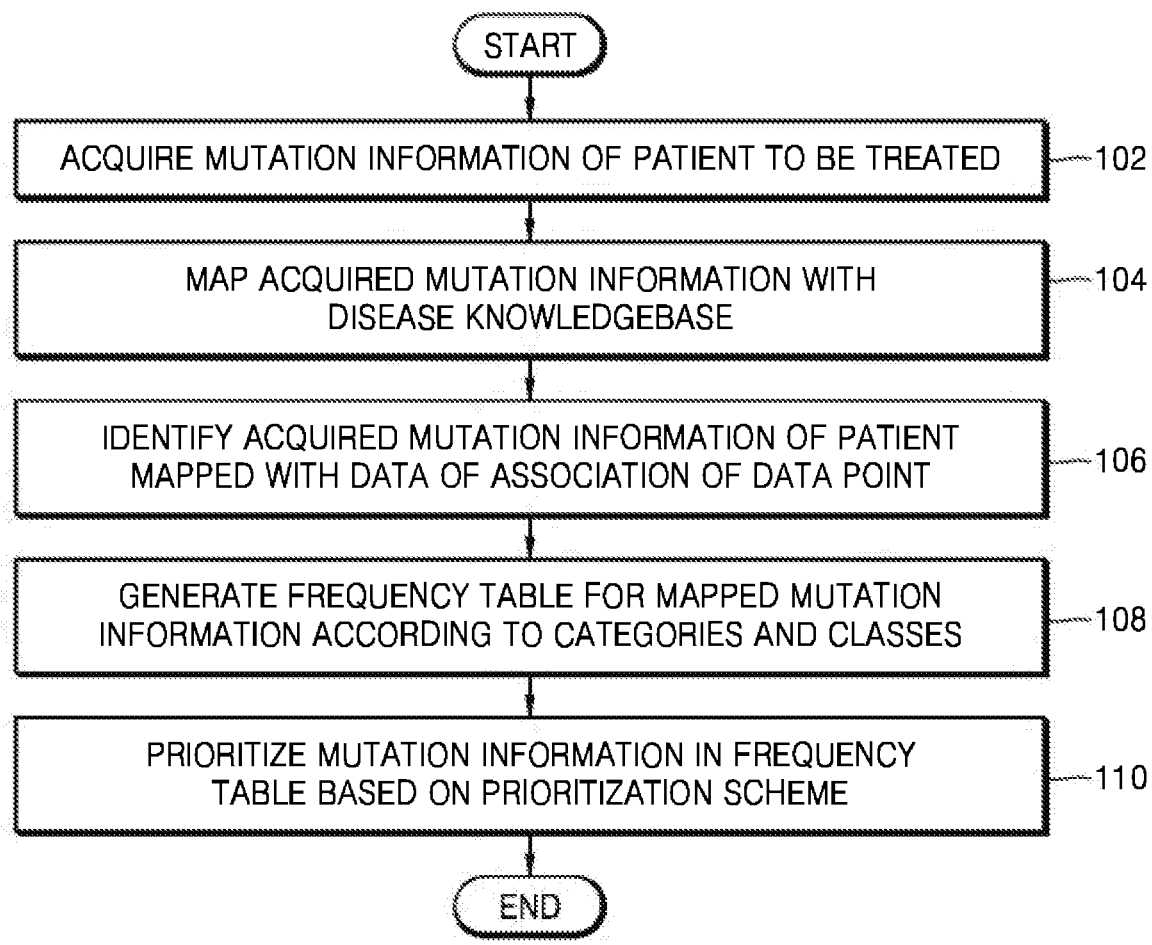
FIG. 1 is a flowchart of a method for mutation prioritization for personalized therapy of a patient, according to an embodiment.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

In the specification, when a region is "connected" to another region, the regions may not only be "directly connected", but may also be "electrically connected" via another device therebetween. Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware, software or a combination of hardware and software.

It will be further understood that the terms "includes", "comprises", "including" and/or "comprising" when used in this specification, specify the presence of stated features, integers, steps, operations, elements and/or components, but do not preclude the presence or addition of one or more other features integers, steps, operations, elements, components, and/or groups thereof. As used herein, the term "and/or" includes any and all combinations of one or more of the associated listed items.

Reference will now be made in detail to embodiments, examples of which are illustrated in the accompanying drawings. In this regard, the present embodiments may have different forms and should not be construed as being limited to the descriptions set forth herein. Accordingly, the embodiments are merely described below, by referring to the figures, to explain aspects.

The term "alteration in genomic DNA" as used herein includes all types of mutations such as, but not limited to, substitutions, insertions, deletions, and frameshifts. The term "alteration of genomic DNA" and "mutation" may be used synonymously in the context of the disclosure.

Mutation Prioritization for Personalized Therapy of Patient

One or more embodiments provide methods and devices for mutation prioritization which is helpful in application of personalized therapy to a patient. In other words, one or more embodiments enable doctors to personalize therapy to be given to a patient. A mutation map of a patient suffering with cancer generally indicates tens to thousands of alterations of genomic DNA. During the process of treating the patient, it is challenging to identify alterations of genomic DNA that are useful for targeted personalized therapy. One or more embodiments address a problem of identifying a most relevant alteration of genomic DNA. One or more embodiments provide a decision support system that sorts alterations of genomic DNA in the patient based on supporting evidences from data gathered from various categories of knowledge sources such as, but not limited to, clinical trials, therapy linkages, and publications. The knowledge source for a clinical trial may include, but is not limited to, ClinicalTrials.gov; the knowledge source for a therapy may include, but is not limited to, Drugs@FDA® and DrugBank®; and the knowledge source for a publication may include, but is not limited to, PubMed® etc. The sorted alterations of genomic DNA in the patient give a fair idea to a medical doctor, a caregiver, or a researcher of how to identify the most relevant mutations that are helpful to clinicians or researchers in making informed decisions.

FIG. 1 is a flowchart of a method for mutation prioritization for personalized therapy of a patient, according to an embodiment.

Figure 2:
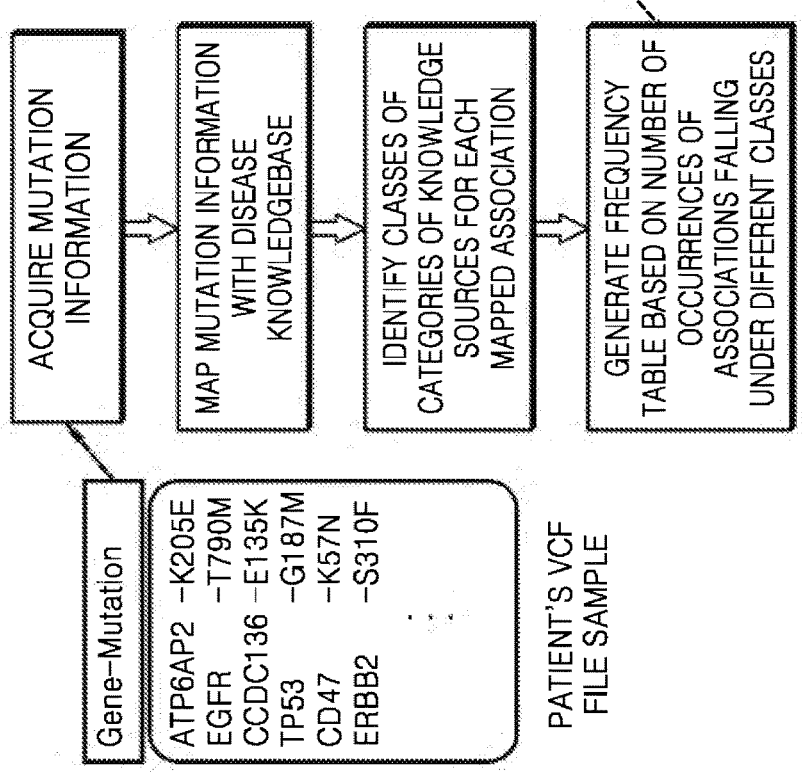
FIG. 2 is a flowchart for describing obtaining of patient's variation data (for example, a variant call format (VCF) file) and generating a frequency table, according to an embodiment.

In operation 102, mutation information of a patient to be treated is acquired. The mutation information includes information associated with a disease, a gene, or an alteration of genomic DNA, as shown in FIG. 2. Generation of mutation information of a patient is performed by methods known in the art. For example, a patient's genome is sequenced and analyzed to identify relevant mutations. Patient variation data, for example, a variant call format (VCF) file, containing the identified mutations may be generated using a standard next generation sequencing (NGS) pipeline.

The acquired mutation information is mapped with a disease knowledgebase in operation 104 to find out if information related to the acquired mutation information is available in the disease knowledgebase. The mapping helps with finding the relevant information available in the disease knowledgebase regarding the acquired mutation information.

The disease knowledgebase may be created beforehand by gathering data from one or more knowledge sources falling under one or more categories. The disease knowledgebase includes data of associations or linkages between a data point indicative of an alteration of genomic DNA, a gene, and a disease derived from the category of the knowledge source with a data point indicative of parameters of clinical relevance from the category of the knowledge source. The parameters of clinical relevance used herein may include a disease stage, a disease type, or a disease sub-type.

The category of the knowledge source is ranked based either on a user input or in any pre-defined priority. Further, the data of associations, for example the relation of a mutation in a gene to a disease, of the data point in the category of the knowledge source is classified into classes pre-defined for each of the categories of the knowledge source with pre-assigned precedence.

Generation of the disease knowledgebase involves curating the gathered data for specific information of <Disease, Gene, Mutation>, also represented as <D, G, M> linkages or <D, G, M> triad, classifying the every <D, G, M> triad (linked data) identified during the curating, and identifying points from the knowledge source linked to the <D, G, M> triad in the knowledgebase. As mentioned, the categories of the knowledge sources (clinical trials, therapy linkages and publications) are ranked either on the basis of a user input or in any pre-defined priority. Therefore, as per ranking assigned to the categories of the knowledge sources, specific data points from the knowledge source may be displayed or presented in the disease knowledgebase. For example, often times, doctors and caregivers may be more interested in specific mutations that may be present in a patient. Treatment options are often decided based on these mutations. Therefore, user preference may be therapies>clinical trials>publications.

The data points falling under any of the three categories (clinical trials, therapies, and publications) of knowledge source are further classified into a plurality of classes pre-defined for each of the category of the knowledge sources, where the classes have pre-assigned precedence.

For example, where clinical trials are selected as one of the categories of the knowledge sources, and associations are identified with a <D, G, M> set (data point). The clinical trial is assigned a specific class for a given <D, G, M> based on its relevance to that <D, G, M>. Additionally, the same clinical trial may also be associated to a different <D, G, M> set and is classified based on its relevance to the different <D, G, M> set. Further, a <D, G, M> set may be associated with multiple data points from a given category of the knowledge source. Further, a <D, G, M> set may be associated with multiple clinical trials. Table 1 illustrates an example of the data of associations for clinical trials forming a disease knowledgebase or part of the disease knowledgebase. Therefore, the classification is relative to <D, G, M> and same holds true for other classification of other categories of knowledge sources. 'ClinicalTrials.gov' provides a unique id/registry number for each clinical trial called the NCTID which is an 8 digit number preceded by the letters 'NCT'. However, Table 1 is provided with dummy unique id/registry numbers for the sake of understanding the data and classification. Every class signifies extent of relevance of a given gene and mutation to a clinical trial for a disease. Classes can be labelled as CT0, CT1, CT2 and CT3, where the CT0 signifies a most relevant class and CT3 signifies a least relevant class.

TABLE 1

| Tumor (Disease) | Gene | Mutation | NCTID | Class |
| --- | --- | --- | --- | --- |
| Breast | ERBB2 | S310F | NCT01827267 | CT1 |
| Breast | ERBB2 | S310F | NCT01670877 | CT1 |
| Breast | ERBB2 | S310F | NCT01953926 | CT1 |
| Breast | ERBB2 | S310F | NCT00730925 | CT1 |
| Breast | ERBB2 | S310F | NCT01288261 | CT2 |
| Breast | ERBB2 | S310F | NCT00580333 | CT2 |
| Breast | ERBB2 | S310F | NCT01271725 | CT3 |
| Breast | ERBB2 | S310F | NCT01441596 | CT3 |
| Breast | ERBB2 | S310F | NCT01531764 | CT3 |

Therapies may be selected on the basis of the knowledge source category. For example, association of <D, G, M> to a drug or a mechanism of drug action through curation of published studies. Classification of therapies may be performed based on the patient mutation and disease information. Classes can be labelled as T0, T1, T2 and T3, where T0 signifies a most relevant class and T3 signifies a least relevant class.

When publications are selected as category of the knowledge source, for a given <D, G, M>, relevant publications are identified. The identified {<D, G, M>, publication} sets are classified into relevant classes based on clinical and pre-clinical statuses of the studies discussed in the publication. Classes can be labelled as P0, P1, P2 and P3, where P0 signifies a most relevant class and P3 signifies a least relevant class. A low class number indicates higher relevance and vice versa, i.e., P0 has higher relevance than P3 and is likewise applicable for the clinical trial (CT), where CT0 has a higher relevance than CT3, and therapy (T), where T0 has a higher relevance than T3.

Operation 106 identifies the alteration of genomic DNA provided in the acquired mutation information of the patient, which was mapped with the data of associations or linkages of the data point. An output of mapping is mapped to mutation information which indicates relevant data points present in the knowledgebase with respect to the acquired mutation information, as will be described below with reference to FIGS. 2 and 3.

In operation 108, a frequency table for the mapped mutation information is generated according to categories of the knowledge source and subsequently according to respective classes. The frequency table includes a plurality of columns, where each column is populated with a number of occurrences of the data of associations or linkages of the data point belonging to a particular class of a category of the knowledge source, and a plurality of rows, where each row is populated with the number of occurrences of data of associations or linkages of the data points linked with a particular alteration of genomic DNA. FIG. 2 is a flowchart for describing obtaining of patient's variation data (for example, a VCF file) and generating a frequency table, according to an embodiment. Numeric values populating the columns of the knowledge sources and its subsequent classes in the frequency table indicate the number of occurrences of the mapped mutation information found that particular class of the knowledge source. For example, for a gene-mutation ATP6AP2-K205E, the column CT1 under clinical trials shows value '1', which signifies that the ATP6AP2-K205E is mapped once in the Class 1 of the clinical trials. Similarly, column CT0 under clinical trials shows value '0', which indicates that the ATP6AP2-K205E is not mapped under the category of Class 0 of clinical trials.

Figure 3:
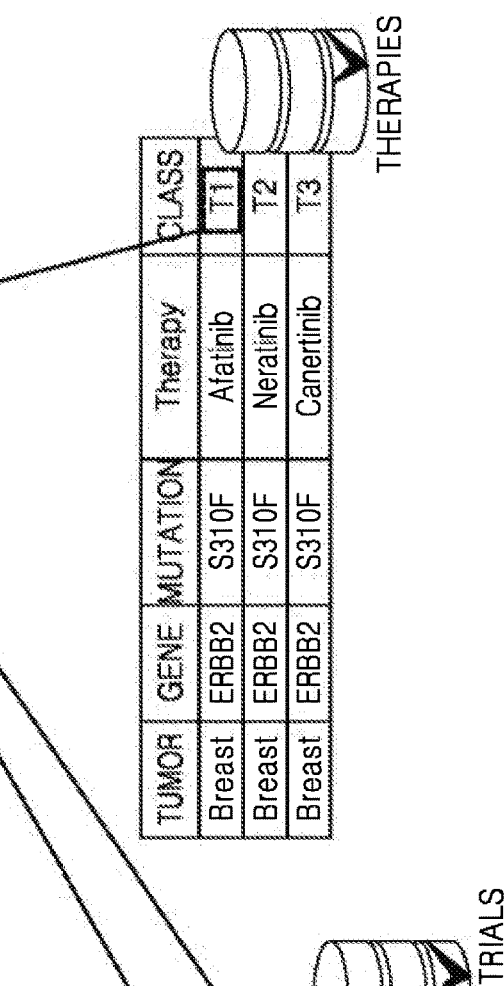
FIG. 3 is a diagram for describing generating of a frequency table from patient's variation data (for example, a VCF file), according to an embodiment.

FIG. 3 is a diagram for describing the generating of the frequency table, according to an embodiment. Table 1 is presented in FIG. 3 for the sake of understanding how the frequency table is generated from the data of associations from clinical trials forming a disease knowledgebase or part of the disease knowledgebase. In this case, two knowledge sources, clinical trials and therapies, are used for generating the frequency table. The gene-mutation ERBB2-S310F is run against the clinical trial knowledgebase (part of the disease knowledgebase), and is found to be mapping four times in class CT1, two times in class CT2, and three times in class CT3. Thereafter, corresponding entries are made in the frequency table against the gene-mutation ERBB2-S310F under the respective columns of the classes. Further, the gene-mutation ERBB2-S310F is also run against the therapy knowledgebase (part of the disease knowledgebase) and is found to be mapping once in class T1, once in class T2 and once in class T3. Thereafter, corresponding entries are made in the frequency table against the gene-mutation ERBB2-S310F under the respective columns of the classes. Likewise, the other gene-mutation identified from patient's VCF is mapped one by one and the frequency table is generated. In an alternative embodiment, all the gene-mutations identified from patient's VCF are taken together for mapping for the purpose of generating the frequency table.

The mapped mutation information in the frequency table is prioritized based on a prioritization scheme in operation 110. There may be various prioritization schemes designed on the basis of user requirement for sorting the frequency table. In one embodiment, a strict criterion may be chosen for selecting data based on a preferred category of the knowledge source as primary filter. This scheme exploits linkages present between various data sources. The scheme provides for:

(a) filtering the frequency table based on one category of the knowledge source selected from the one or more categories of the knowledge sources;

(b) populating the filtered frequency table with data points of the one or more categories of the knowledge source not selected in the filtering, and linking those with data points associated with the selected category of the knowledge source; and (c) sorting the frequency table based on the number of occurrence of the data point viz a viz ranking of the category of the knowledge source and pre-assigned precedence of the class of the data point present in respective category of the knowledge sources.

Figure 4A:
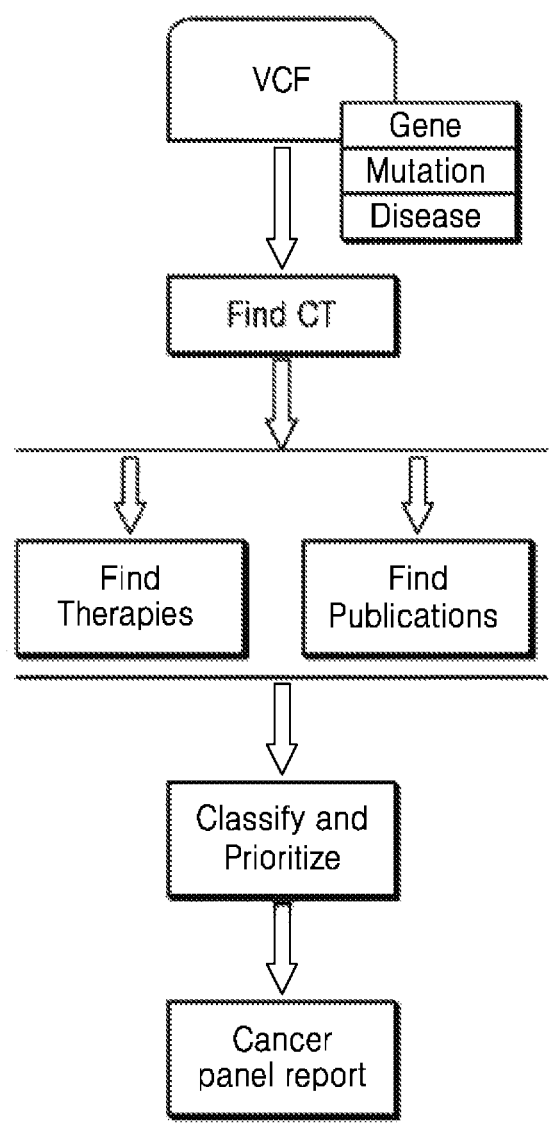
FIGS. 4A and 4B are flowcharts for describing two prioritization schemes, according to an embodiment.

In an embodiment of the prioritization scheme, clinical trials (category of the knowledge source) may be chosen as a primary filter. The frequency table generated (for example, in operation 108) is filtered based on clinical trials so as to list out only such mutation information of the patient which are showing corresponding entries in any of the classes of the clinical trial section of the frequency table. In a next operation, only such data points of the other categories of the knowledge sources (namely therapies and publications) which are related or linked with the identified data points of clinical trials in the previous operation are selected and the frequency table is populated accordingly. In a final operation, the entries in the frequency table are sorted by giving higher ranking to the gene-mutations indicating higher entries under the corresponding classes. The ranking of the gene-mutations is performed while taking into consideration the ranks assigned to the knowledge sources and the precedence assigned to the classes falling under those knowledge sources (refer to FIG. 4A).

Figure 4B:
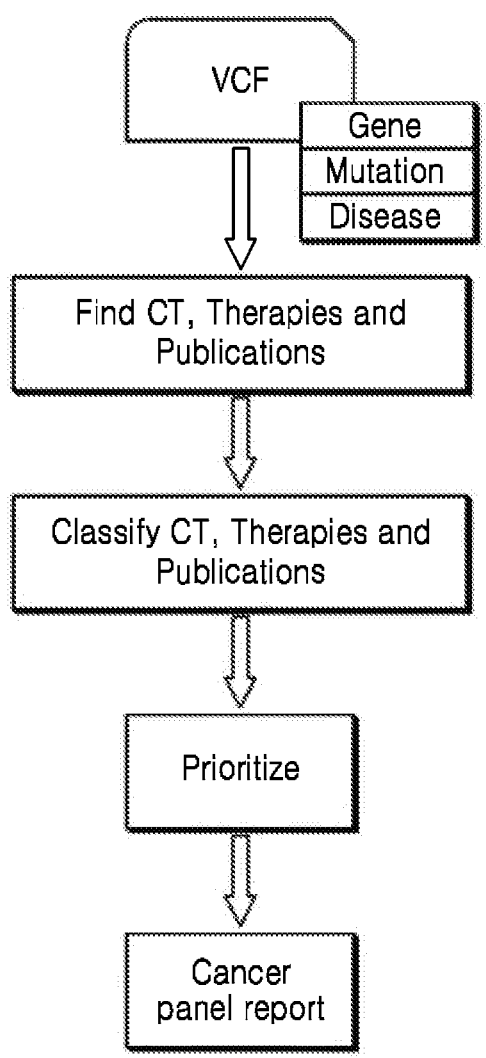

In another embodiment, the prioritization scheme provides for sorting the frequency table while considering all evidences present for a given mutation independently (refer to FIG. 4B):

(a) Arranging the linked data points in the frequency table according to categories of the knowledge source and subsequently according to respective classes; and (b) Sorting the frequency table for the mapped mutation information based on the number of occurrence of the data points viz a viz ranking of the category of the knowledge sources and pre-assigned precedence of the classes of the data points present in respective category of the knowledge sources.

In one embodiment, a sorting technique may use multi-level sort and below is a representation of such sorting (FIG. 5). Each mutation is assigned a score S(m), wherein S(m) is defined according to Equation 1 below.

$$S(m) = F(\{CT0,CT1,CT2,CT3\},\{T0,T1,T2,T3\},\{P0,P1,P2,P3\}) \qquad (1)$$

And S(m) is computed according to Equation 2 below.

$$S(m) = \sum_{i=0}^{k-1} \left( \sum_{j=0}^{c-1} N_{ij} \times 10^{(c-1-j)t} \right) \times 10^{t(k-1-i)} \qquad (2)$$

Where, k denotes a number of categories of the knowledge sources, c denotes a total number of classes for each category of the knowledge sources (for example c=4 for Class 0 to 3), $N_{ij}$ denotes represents the number of data points belonging to category of the knowledge sources i and Class j, and t is chosen so that $10^t$ represents a maximum number of data points per class.

In an embodiment of the prioritization scheme, the sorting is performed while considering the clinical trials and the therapies independently. Data filtration is performed independently on both the clinical trials and the therapies. However, it is to be appreciated that this may be extended over any number categories of knowledge sources. In an embodiment, the clinical trials are ranked higher in comparison to the therapies (Clinical trial>Therapies). The frequency table generated after operation 108 is sorted as per the prioritization scheme (FIG. 5). After the sorting, the row numbers 6 and 7 are presented at top of the sorted frequency table. Here, Row #6 has evidence scores 4, 2, 3, 4, 5, 4, 3, 2, and Row #7 has evidence scores 5, 2, 3, 4, 5, 2, 3, 1.

Thereafter, based on a simple sorting mechanism, the sorted order for these two entries would be Row #7 and Row #6.

In alternative embodiment of the prioritization scheme, the therapies are ranked higher as compared to the clinical trials (Therapies>Clinical trials) (FIG. 6). After the sorting, the row numbers 6 and 7 are presented at the top of the sorted table. Here, Row #6 has evidence scores for clinical trials=4, 2, 3, 4 and therapies=5, 4, 3, 2. Row #7 has evidence scores for clinical trials=5, 2, 3, 4 and therapies= 5, 2, 3, 1.

In this scenario since the higher priority is given to therapy classes. Hence, according to the evidence order, Row #6 has evidence scores 5, 4, 3, 2, 4, 2, 3, 4, and Row #7 has evidence scores 5, 2, 3, 1, 5, 2, 3, 4.

In this case, based on a simple sorting mechanism the sorted order for these two entries would be Row #6 and Row #7.

It is to be understood that the ranking of the different knowledge sources used in the one or more embodiments depends on the requirement of user. Once the sorted frequency table is generated, it becomes easy for the doctors to choose the correct way to personalize a therapy for the patient based on the evidences or information made available.

Figure 7:
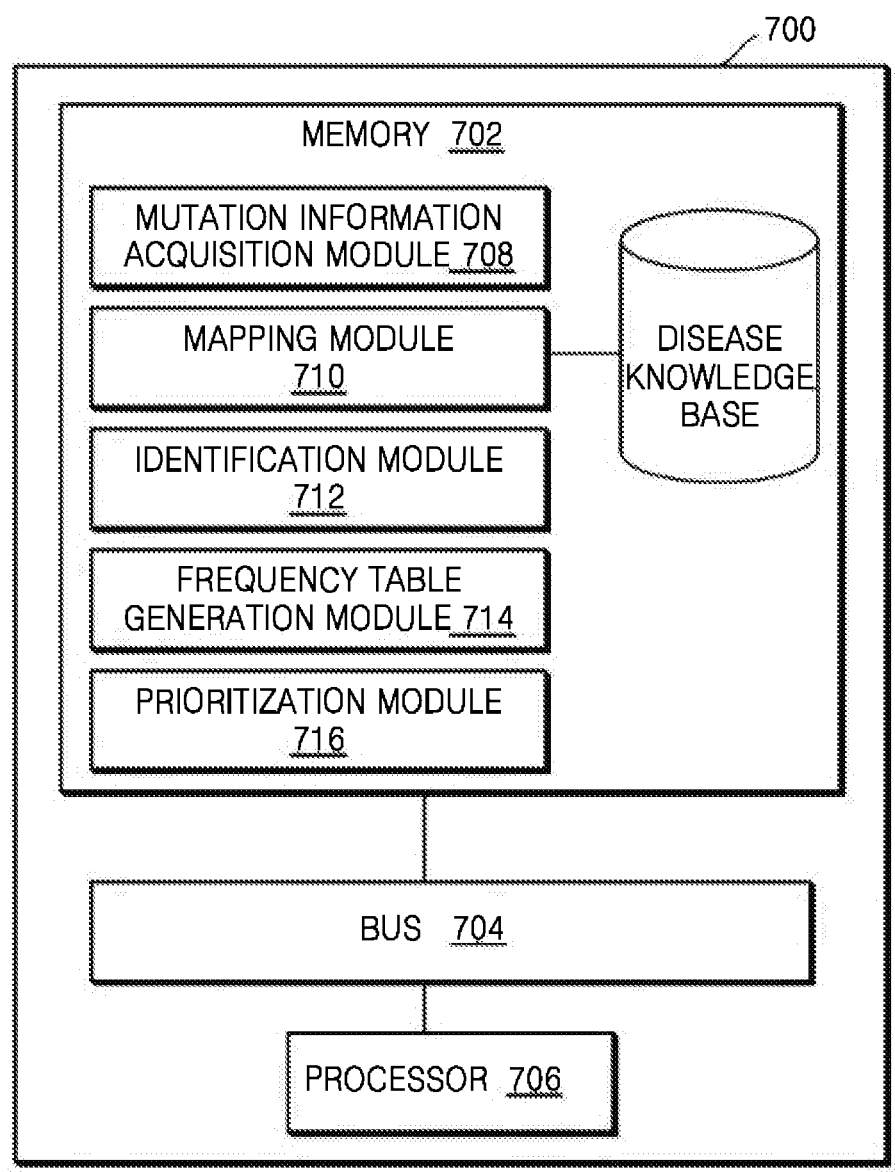
FIG. 7 is a block diagram of a device for mutation prioritization for personalized therapy of one or more patients, according to an embodiment.

One or more embodiments also provide a device for mutation prioritization for personalized therapy of a patient. FIG. 7 is a block diagram of a device 700 for mutation prioritization for personalized therapy of one or more patients, according to an embodiment. The device 700 is configured to prioritize the mapped mutation information and thereby to generate a list of prioritized mutations for perusal by doctors or care givers.

The device 700 includes a processor 706 and a memory 702 connected to the processor 706.

The processor 706 may be realized by any type of a computational circuit, such as, but not limited to, a microprocessor, a microcontroller, a complex instruction set computing (CISC) microprocessor, a reduced instruction set computing (RISC) microprocessor, a very long instruction word (VLIW) microprocessor, an explicitly parallel instruction computing (EPIC) microprocessor, a digital signal processor (DSP), any other type of processing circuit, or a combination thereof.

The memory 702 includes a plurality of modules stored in the form of executable program which instructs the processor 706 to perform the method illustrated in FIG. 1. The memory 702 may include a mutation information acquisition module 708, a mapping module 710, an identification module 712, a frequency table generation module 714, and a prioritization module 716. The memory 702 may also include the disease knowledgebase. Alternatively, the disease knowledgebase may be communicatively coupled to the device 700 through any type of communication.

Computer memory elements may include a suitable memory device for storing data and executable program, such as a read only memory (ROM), a random access memory (RAM), an erasable programmable read only memory (EPROM), an electrically erasable programmable read only memory (EEPROM), a hard drive, or a removable media drive for handling memory cards. One or more embodiments may be implemented in conjunction with program modules, including functions, procedures, data structures, and application programs, for performing tasks, or defining abstract data types or low-level hardware contexts. An executable program stored on any of the above-mentioned storage medium may be executable by the processor 706.

The mutation information acquisition module 708 instructs the processor 706 to perform operation 102 of FIG. 1.

The mapping module 710 instructs the processor 706 to perform operation 104 of FIG. 1.

The identification module 712 instructs the processor 706 to perform operation 106 of FIG. 1.

The frequency table generation module 714 instructs the processor 706 to perform operation 108 of FIG. 1.

The prioritization module 716 instructs the processor 706 to perform operation 110 of FIG. 1.

Disease Knowledgebase and Method of Generating the Same

One or more embodiments also provide a method for generating a disease knowledgebase. Operations of the method broadly include aggregation of raw data from various public data sources into a local repository. Also, the operations include cleaning and curating aggregated data collecting specific information (<Disease, Gene, Mutation> and data of clinical relevance) as data points, and identifying associations between the data points. Such curated information/data point associations are then classified according to classification rules to generate the disease knowledgebase. Therefore, the disease knowledgebase includes various knowledge sources linked to three primary categories: clinical trials, therapies, and publications. The clinical trials, therapies, and publication knowledge sources are independently curated and classified. Further, the classification rules for the respective categories (clinical trials, therapies, and publications) of the knowledge sources are designed as per the requirement of the user. Hence, there may be differences between classification of data points falling under clinical trials as compared to the therapies or publications.

Figure 8:
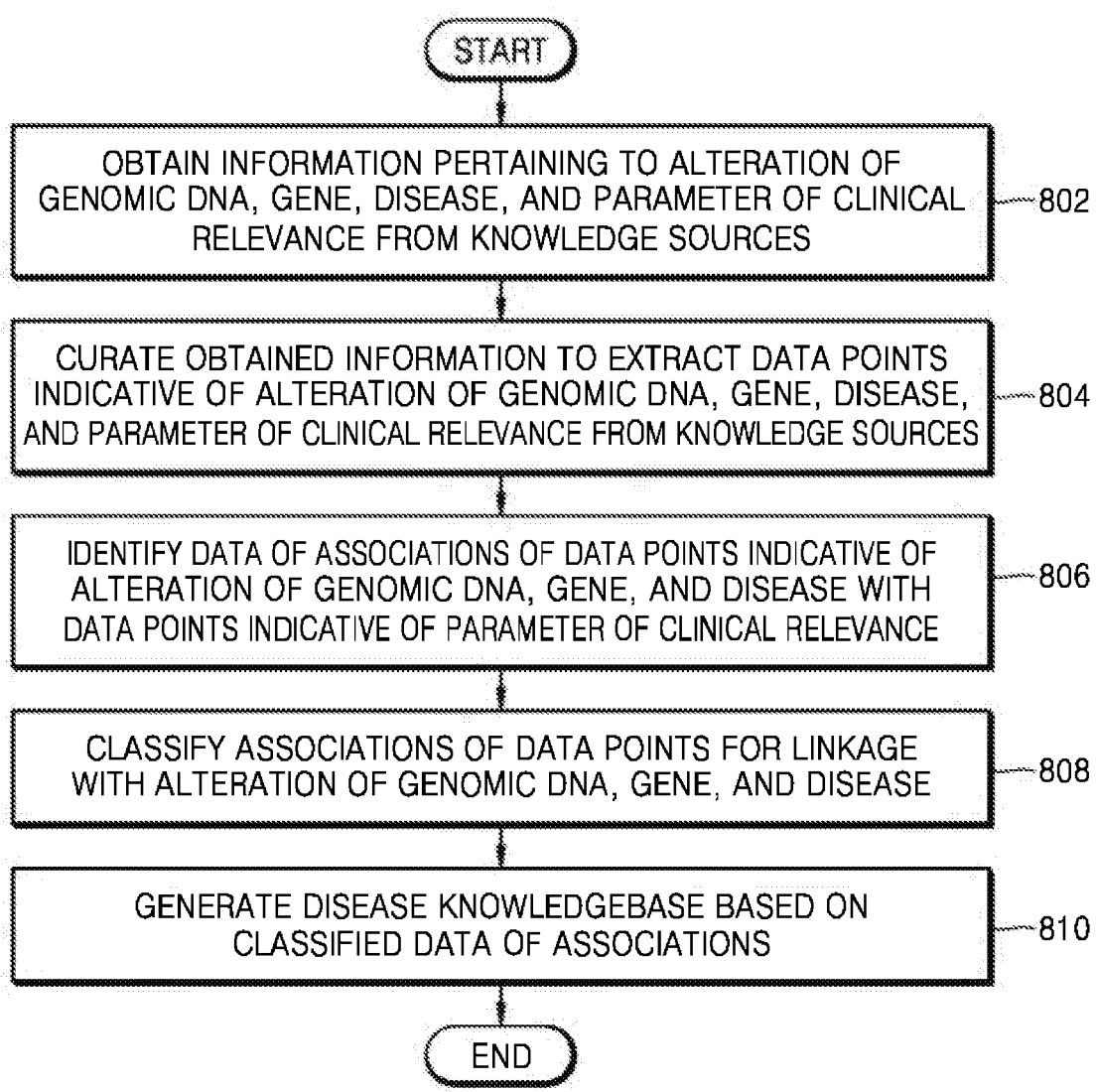
FIG. 8 is a flowchart of a method for generating a disease knowledgebase, according to one embodiment.

FIG. 8 is a flowchart of a method for generating a disease knowledgebase, according to one embodiment.

Information pertaining to an alteration of genomic DNA, a gene, a disease, and a parameter of clinical relevance from various knowledge sources is obtained in operation 802.

The obtained information is curated to extract data points indicative of the alteration of genomic DNA, the gene, the disease, and the parameter of clinical relevance from knowledge sources, in operation 804. Therefore, after curating, broadly two sets of data points are generated. For example, one set for data points may be indicative of the alteration of genomic DNA, the gene, and the disease, while another set for data points may be indicative of the parameter of clinical relevance.

The data of associations of the data points indicative of the alteration of genomic DNA, the gene, and the disease with the data points indicative of the parameter of clinical relevance are identified in operation 806. For example, a data point of Breast tumour: ERBB2: S310F <DGM> may find a match with a clinical trial where the inclusion criteria covers the breast cancer related to gene ERBB2 and associated mutation S310F.

The data points in the knowledge sources associated with <DGM> are classified into a plurality of classes in operation 808. Operation 808 involves classifying the association of the data points for linkage with the disease, the gene, and the alteration of genomic DNA into knowledge source categories, and then into classes. A class is assigned to each of the data points for linkage with the disease, the gene, and the alteration of genomic DNA. Therefore, this classification is relative to each <D, G, M> set. So if a given data point is associated with multiple data points (<DGM> sets) from a given knowledge source, then the given data point may have a different classification for each <D, G, M>, as discussed previously under the section dealing with mutation prioritization for personalized therapy of patient. The classes are predefined for each of the categories of the knowledge sources with pre-assigned precedence. Further, the categories of the knowledge sources are also ranked based on user input or a pre-defined priority. The classification of the data points fall under three primary categories: clinical trials, therapies, and publications of the various knowledge sources is done on the similar way as explained above with reference to FIG. 1, etc.

Figure 9:
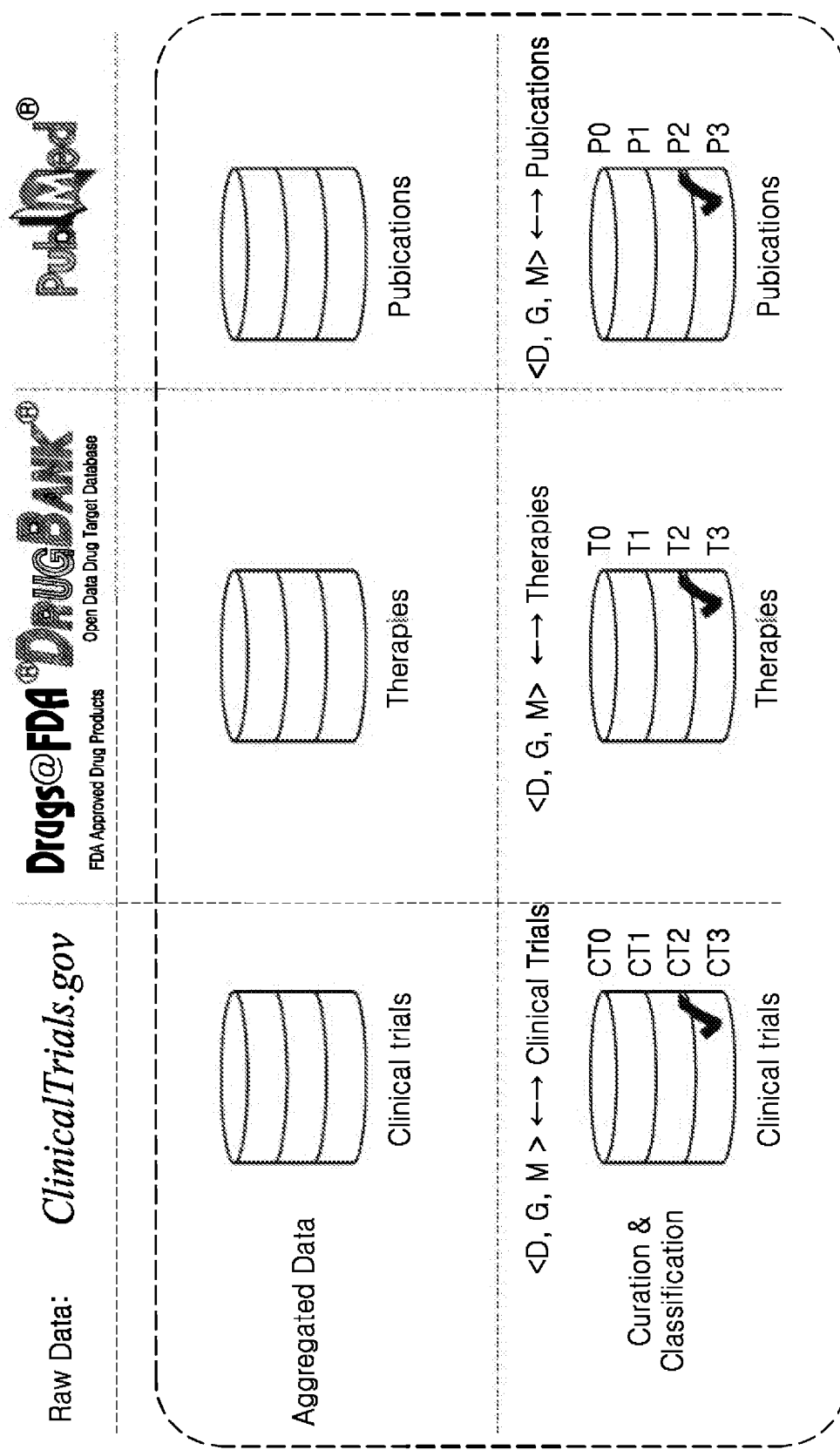
FIG. 9 is a diagram for describing obtaining and aggregating of data from a plurality of categories of knowledge sources, curating of the data to obtain data points, and classifying of the data points, according to one embodiment.

FIG. 9 is a diagram for describing the obtaining and aggregating of the data from a plurality of categories of knowledge sources, the curating of the data to obtain data points, and the classifying of the data points, according to one embodiment.

The disease knowledgebase is generated based on one or more data points classified into one or more categories of knowledge sources in operation 810. The generated disease knowledgebase includes, according to the categories of the knowledge source and subsequently respective classes, arrangement of data of associations of data points indicative of the alteration of genomic DNA, the gene, and the disease derived from the knowledge source with data points indicative of the parameter of clinical relevance from knowledge source.

Classification rules for classifying data points falling under clinical trials, therapies, and publications for each scenario will now be described.

(A) Clinical Trials

The <D, G, M> set (the data point) identified from a clinical trial is assigned a specific class, where every class signifies an extent of relevance of a given gene and mutation to a clinical trial for a disease. Classes are labelled as CT0, CT1, CT2, and CT3, and the precedence assigned to the classes makes CT0 a most relevant class while CT3 as a least relevant class. Classification rules for clinical trials are listed in Table 2. It is to be understood that the definition of the classes provided in Table 2 are examples of indicative of the parameters of clinical relevance. For example, a data point indicating information for <G,M> is included in Class CT0.

TABLE 2

| Class ID | Definition |
| --- | --- |
| CT0 | Given <Gene, Mutation> is specified in inclusion criteria |
| CT1 | Existence of mutation in the gene is specified in the inclusion criteria |
| CT2 | Mutation in the gene is not specified, clinical trial might be for retrospective subgroup analysis |
| CT3 | Drug mechanism might be related to the gene |

(B) Therapies

The association of <D, G, M> to drug or drug action is done through curation of published studies. Approval status (on-label/off-label) of a given drug is obtained using USFDA drug label information. The classification of therapies is performed based on the acquired mutation and disease information. As therapy classification is dependent on patient specific information, it is performed while processing patients' data. Classes are labelled as T0, T1, T2 and T3, and the precedence assigned to the classes indicates T0 is a most relevant class while T3 is a least relevant class. It is to be understood that the definition of the classes provided in Table 3 are examples indicative of the parameters of clinical relevance. Example classification rules for therapy are listed in Table 3. For example, a data point indicating approved therapy for <G,M> in a given patient's cancer type is put under the class T0.

TABLE 3

| Class ID | Definition |
| --- | --- |
| T0 | Approved therapy for {gene, mutation} in patients' cancer type |
| T1 | Approved therapy for {gene, mutation} in other cancer type |
| T2 | Experimental therapy for {gene, mutation} in patients' cancer type |
| T3 | Experimental therapy for {gene, mutation} in other cancer type |

(C) Publications

For a given <D, G, M>, relevant publications are identified. The identified {<D, G, M>, publication} sets are classified into relevant classes based on the clinical, pre-clinical status of the studies discussed in the publication. It is to be understood that the definition of the classes provided in Table 4 are examples indicative of the parameters of clinical relevance. The classes are labelled as P0, P1, P2 and P3 and the precedence assigned to the classes where P0 is a most relevant class while P3 is a least relevant class. Example classification rules for publications are listed in Table 4.

TABLE 4

| Class ID | Definition |
| --- | --- |
| P0 | Pre-clinical and clinical studies are in agreement on the use of therapy for a given <D, G, M> |
| P1 | Only clinical studies available on the use of a therapy for a given <D, G, M> |
| P2 | Only pre-clinical studies are available on the use of a therapy for a given <D, G, M> |
| P3 | Neither pre-clinical nor clinical studies are available for a given <D, G, M> |

As per the example rules, a data point indicating that the pre-clinical and clinical studies are in agreement on the use of a therapy for a given <D, G, M> is put under the class P0.

One or more embodiments further provide additional classification criteria apart from those discussed above so as to create more fine tuned classification rules.

Apart from the main classifications provided in previous description, below criteria could be used for additional classification of classes of the knowledge source categories and fine grained prioritization.

(a) Location Based Classification for Clinical Trials

In an embodiment, relevance is assigned to a clinical trial based on a geographic location of the clinical trial, where the various relevant geographical locations for the patient to be treated are given precedence based on the user input (for example, a $1^{st}$ preference, a $2^{nd}$ preference, a $3^{rd}$ preference, and so on).

(b) Drug Action Based Classification for Therapies

In an embodiment, a drug action such as "Sensitive, Resistant, No Effect" on a given gene or mutation is used as an additional filter to sort the frequency table.

One or more embodiments also provide a device for generating a disease knowledgebase.

Figure 10:
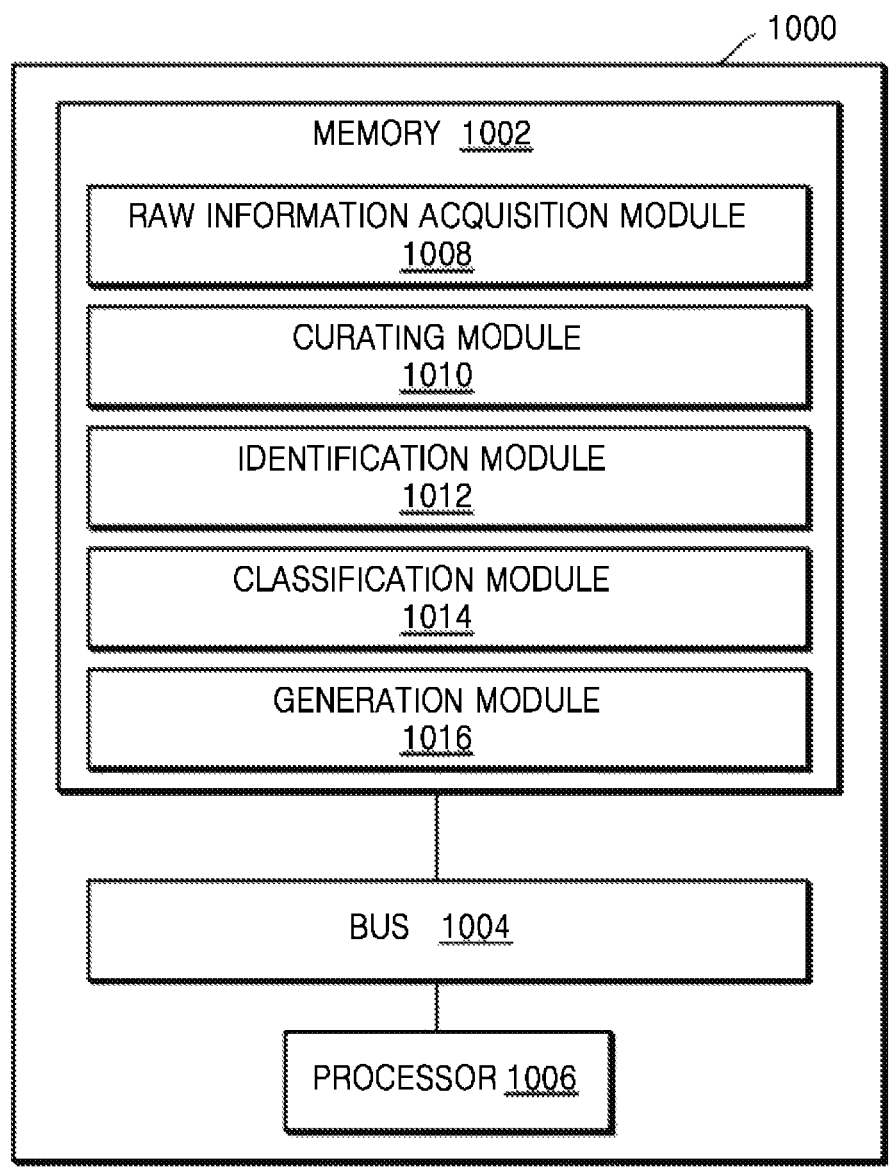
FIG. 10 is a block diagram of a device for generating a disease knowledgebase, according to an embodiment.

FIG. 10 is a block diagram of a device 1000 for generating a disease knowledgebase, according to an embodiment. The device 1000 is configured to generate the disease knowledgebase based on acquired raw data.

The device 1000 includes a processor 1006 and a memory 1002 coupled to the processor 1006.

The processor 1006 may be realized by any type of a computational circuit, such as, but not limited to, a microprocessor, a microcontroller, a CISC microprocessor, an RISC microprocessor, a VLIW microprocessor, an EPIC microprocessor, a digital signal processor, any other type of processing circuit, or a combination thereof.

The memory 1002 includes a plurality of modules stored in a form of executable program which instructs the processor 1006 to perform the method of FIG. 8. The memory 1002 may include a raw information acquisition module 1008, a curating module 1010, an identification module 1012, a classification module 1014, and a generation module 1016.

Computer memory elements may include a suitable memory device for storing data and executable program, such as ROM, RAM, EPROM, EEPROM, a hard drive, a removable media drive for handling memory cards and the like. One or more embodiments may be implemented in conjunction with program modules, including functions, procedures, data structures, and application programs, for performing tasks, or defining abstract data types or low-level hardware contexts. An executable program stored on any of the above-mentioned storage media may be executable by the processor 1006.

The raw information acquisition module 1008 instructs the processor 1006 to perform operation 802 of FIG. 8.

The curating module 1010 instructs the processor 1006 to perform operation 804 of FIG. 8.

The identification module 1012 instructs the processor 1006 to perform operation 806 of FIG. 8.

The classification module 1014 instructs the processor 1006 to perform operation 808 of FIG. 8.

The generation module 1016 instructs the processor 1006 to perform operation 810 of FIG. 8.

The device described herein may include a processor, a memory for storing program data and executing it, a permanent storage such as a disk drive, a communications port for handling communications with external devices, and user interface devices, including a display, keys, etc. When software modules are involved, these software modules may be stored as program instructions or computer-readable codes executable on the processor on a computer-readable media including read-only memory (ROM), random-access memory (RAM), CD-ROMs, magnetic tapes, floppy disks, and optical data storage devices. The computer-readable recording medium can also be distributed over network coupled computer systems so that the computer-readable code is stored and executed in a distributed fashion. This media can be read by the computer, stored in the memory, and executed by the processor.

The one or more embodiments may be described in terms of functional block components and various processing steps. Such functional blocks may be realized by any number of hardware and/or software components configured to perform the specified functions. For example, the one or more embodiments may employ various integrated circuit components, e.g., memory elements, processing elements, logic elements, look-up tables, which may carry out a variety of functions under the control of one or more microprocessors or other control devices. Similarly, where the elements of the one or more embodiments are implemented using software programming or software elements, the disclosure may be implemented with any programming or scripting language, including C, C++, Java, and assembler, with the various algorithms being implemented with any combination of data structures, objects, processes, routines or other programming elements. Functional aspects may be implemented in algorithms that execute on one or more processors. Furthermore, the one or more embodiments could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the disclosure and are not intended to otherwise limit the scope of the disclosure in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a", "an", and "the" and similar referents in the context of describing the disclosure (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A computer-implemented method for mutation prioritization for personalized therapy, the method comprising the steps, implemented in one or more processors, of:
    acquiring mutation information of a patient to be treated, wherein the mutation information comprises information associated with at least one of a disease, a gene, and an alteration of genomic DNA;
    generating a VCF (variant call format) file including the acquired mutation information of the patient;
    mapping the acquired mutation information included in the VCF file with a disease knowledgebase, wherein the disease knowledgebase is pre-generated by receiving data from one or more external knowledge sources;
    forming mapped mutation information by identifying at least one of the disease, the gene, and the alteration of genomic DNA, the mapped mutation information being mapped with data points in the disease knowledgebase;
    generating a frequency table according to categories of a knowledge source and classes in the categories, based on the mapped mutation information; and prioritizing the mapped mutation information in the frequency table based on a prioritization scheme,
wherein the disease knowledgebase comprises data of associations of a least one data point indicative of at least one of: at least one disease, at least one gene, and at least one alteration of genomic DNA derived from at least one knowledge source falling under at least one category with at least one data point indicative of a parameter of clinical relevance,
wherein the data associations are classified into a plurality of cases pre-defined according to each of the at least one category of the at least one knowledge source, where the classes have pre-assigned precedence,
wherein the prioritizing the mapped mutation information in the frequency table based on the prioritization scheme comprises:
filtering the frequency table based on one category selected from the at least one category of the at least one knowledge source;
populating the filtered frequency table with data points of the at least one category of the at least one knowledge source not selected during the filtering, the data points being linked with at least one data point associated with the selected category of the at least one knowledge source; and
sorting entries in the frequency table according to rankings of the entries based on the number of occurrences of the at least one data point vis a vis ranking of the at least one category of the at least one knowledge source and the pre-assigned precedence of the classes of the association of the at least one data point of the entries in the frequency table, and
wherein the entries in the frequency table are sorted by giving higher ranking to the mutation information indicating higher entries under the classes.

2. The method of claim 1, wherein the at least one category of the at least one knowledge source comprises a clinical trial category, a therapy category, or a publication category.

3. The method of claim 1, wherein the frequency table comprises:
a plurality of columns, wherein each of the plurality of columns is populated with a number of occurrences of the data of associations of the at least one data point belonging to a particular class of a category of the at least one knowledge source; and
a plurality of rows, wherein each of the plurality of rows is populated with the number of occurrences of the data of associations of the at least one data point linked with a particular alteration of genomic DNA.

4. The method of claim 1, wherein the prioritizing the mapped mutation information in the frequency table based on the prioritization scheme comprises:
arranging data points linked each other in the frequency table according to categories and subsequently respective classes; and
sorting the frequency table for the mapped mutation information based on a number of occurrences of the at least one data point vis a vis ranking of the at least one category of the at least one knowledge source and the pre-assigned precedence of the classes of the association of the at least one data point.

5. The method of claim 1, wherein the at least one category of the at least one knowledge source is ranked based on one of a user input and a pre-defined priority.

6. A device for mutation prioritization for personalized therapy, the device comprising:
a memory; and
at least one processor coupled to the memory,
wherein the at least one processor is configured to:
acquire mutation information of a patient to be treated, wherein the mutation information comprises information associated with at least one of a disease, a gene, and an alteration of genomic DNA;
generate a VCF (variant call format) file including the acquired mutation information of the patient;
map the acquired mutation information included in the VCF file with a disease knowledgebase, wherein the disease knowledgebase is pre-generating by receiving data from one or more external knowledge sources;
form mapped mutation information by identifying at least one of the disease, the gene, and the alteration of genomic DNA, the mapped mutation information being mapped with data points in the disease knowledgebase;
generate a frequency table according to categories of a knowledge source and classes in the categories, based on the mapped mutation information; and
prioritize the mapped mutation information in the frequency table based on a prioritization scheme,
wherein the disease knowledgebase comprises data of associations of at least one data point indicative of at least one of: at least one disease, at least one gene, and at least one alteration of genomic DNA derived from at least one knowledge source falling under at least one category with at least one data point indicative of a parameter of clinical relevance,
wherein the data of associations are classified into a plurality of classes pre-defined according to each of the at least one category of the at least one knowledge source, where the classes have pre-assigned precedence,
wherein the prioritization scheme comprises:
filtering the frequency table based on one category selected from the at least one category of the at least one knowledge source;
populating the filtered frequency table with data points of the at least one category of the at least one knowledge source not selected during the filtering, the data points being linked with at least one data point associated with the selected category of the at least one knowledge source; and
sorting entries in the frequency table according to rankings of the entries based on the number of occurrences of the at least one data point vis a vis ranking of the at least one category of the at least one knowledge source and the pre-assigned precedence of the classes of the association of the at least one data point of the entries in the frequency table, and
wherein the entries in the frequency table are sorted by giving higher ranking to the mutation information indicating higher entries under the classes.

7. The device of claim 6, wherein the at least one category of the at least one knowledge source comprises a clinical trial category, a therapy category, or a publication category.

* * * * *